United States Patent [19]

Archer

[11] Patent Number: 4,875,228

[45] Date of Patent: Oct. 17, 1989

[54] X-RAY GANTRY

[75] Inventor: David Archer, Ontario, Canada

[73] Assignee: Davru Manufacturing Ltd., Mallorytown, Canada

[21] Appl. No.: 218,157

[22] Filed: Jul. 12, 1988

[51] Int. Cl.$^4$ ............................ G01N 23/18; G62D 39/00
[52] U.S. Cl. ...................................... 378/197; 378/193; 378/167
[58] Field of Search .............................. 378/193–198, 378/177, 4, 19, 167, 204, 208; 254/2 R, 133 R, 100, DIG. 4

[56] References Cited

U.S. PATENT DOCUMENTS

| | | | |
|---|---|---|---|
| 1,775,853 | 9/1928 | Goldfield | 378/197 |
| 1,876,737 | 2/1932 | Opp . | |
| 2,798,958 | 1/1956 | Hudson et al. | 378/197 |
| 2,831,123 | 7/1958 | Daly . | |
| 2,968,732 | 4/1959 | Foderaro | 378/197 |
| 4,166,602 | 9/1979 | Nilsen et al. | 378/197 |
| 4,181,347 | 1/1980 | Clark . | |
| 4,503,552 | 3/1985 | Miyahara . | |
| 4,628,524 | 12/1986 | Hepke | 378/197 |
| 4,694,481 | 9/1987 | Tashjian et al. . | |
| 4,716,581 | 12/1987 | Barud . | |
| 4,727,564 | 2/1988 | Mekker et al. | 378/197 |

FOREIGN PATENT DOCUMENTS

| | | | |
|---|---|---|---|
| 1213565 | 3/1966 | Fed. Rep. of Germany . | |
| 57-201842 | 10/1982 | Japan . | |
| 0201841 | 12/1982 | Japan | 378/198 |
| 8703795 | 6/1987 | World Int. Prop. O. | 378/197 |

Primary Examiner—Carolyn E. Fields
Assistant Examiner—Joseph A. Hynds
Attorney, Agent, or Firm—Pennie & Edmonds

[57] ABSTRACT

An improved gantry for an examination apparatus, such as an x-ray apparatus comprising a source of x-rays and a detector of fluoresced photons, is disclosed. The apparatus is particularly suitable for use in a vehicle such that the examination can be carried out at locations convenient to the patients. The apparatus comprises a vertical standard and first and second carriages. The first carriage is movable along the vertical standard and carries a horizontal arm. The horizontal arm carries the second carriage, which moves along the horizontal arm in a direction orthogonal to the axis of the standard. A transverse arm carrying the x-ray apparatus is carried by the second carriage and moves with respect thereto in a third direction orthogonal to the first and second directions, so that three directions of motion along orthogonal axes are thus provided. Additionally, the second carriage is rotatable about the horizontal arm providing a first direction of rotation. The x-ray apparatus is mounted on a support plate which is pivotable with respect to the transverse arm, providing a second degree of rotation. Caging arms are provided which extend from the frame of the vehicle directly to the support plate and are readily fixed thereto, to confine the support table and the associated x-ray apparatus in transit. The caging arms and the standard are shock mounted to the vehicle such that any vibration occurring during travel is damped out.

20 Claims, 3 Drawing Sheets

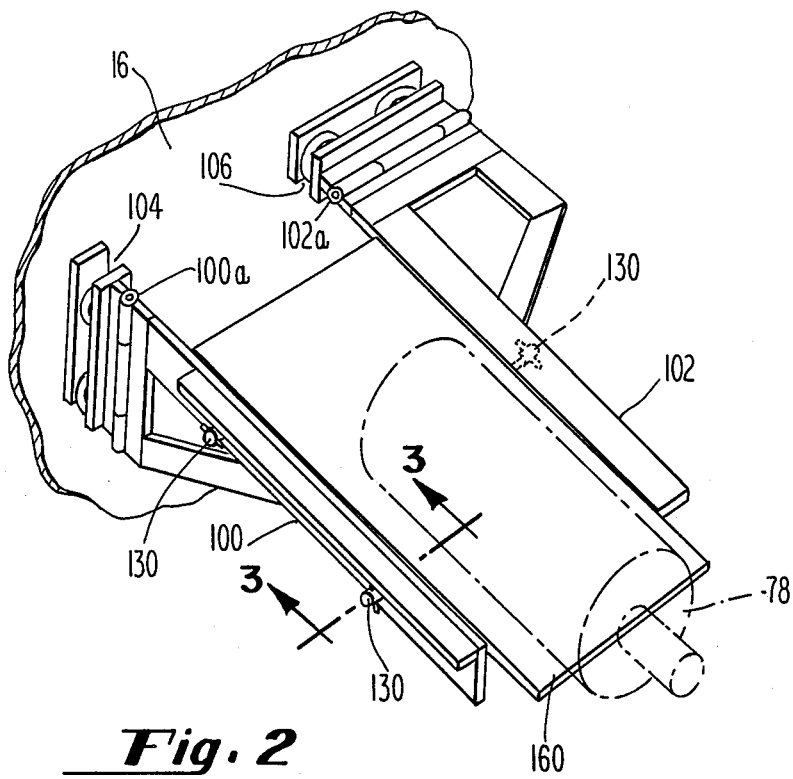
_Fig. 2_
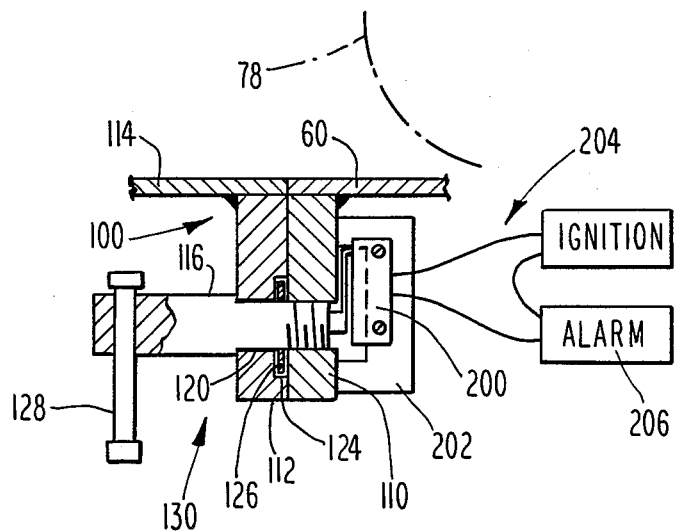
_Fig. 3_

X-RAY GANTRY

FIELD OF THE INVENTION

This invention relates to an improved apparatus for positioning an inspection device with respect to an object to be inspected. More particularly, this application relates to an improved apparatus for positioning a source of x-rays and a detector of fluoresced photons in precise juxtaposition to a limb of a patient to be examined.

BACKGROUND OF THE INVENTION

There has recently been developed a new x-ray fluorescence technique for determining the amount of lead borne in the skeletons of patients. This technique involves exposing the patient to a quantity of low energy x-rays, and detection and spectral analysis of photons fluoresced from the bone. See Wielopolski et al, "Feasibility of non-invasive analysis of lead in the human tibia by soft x-ray fluorescence," Med. Phys. 10(2), March/April 1983, pp. 248-251. Conveniently, the source and detector are juxtaposed to the tibia of a patient. The patient is seated in a chair with one leg extended forward and held in position The source and detector must be juxtaposed to a tibia at a predetermined angle with respect to one another, typically 90 degrees and at a predetermined spacing from the tibia, such that the amount of photons fluoresced can readily be correlated with those from other patients.

The present invention concerns an apparatus for supporting the source of x-rays and detector in precisely the desired position with respect to the tibia of the patient, such that the measurement can be made.

The x-ray fluorescence method of measurement of skeletal lead burden described above is considered to be a very significant improvement in diagnosis of lead toxicity in children. Lead toxicity is a major health problem in children, so that it is desired to provide x-ray fluorescence testing for large numbers of children in a convenient and expedient manner. To this end, it is desired to outfit a mobile van with a complete test apparatus, including the x-ray source and detector, and associated data processing equipment to analyze the results, so that this can be taken to an industrial site or community center or the like and used to perform the testing where convenient, such that a reasonably complete examination of the community can be anticipated.

To mount x-ray apparatus in a vehicle for such purposes is not a simple task. In particular, the apparatus must be mounted in such a way that it is securely held in a safe position and not damaged during travel of the vehicle from place to place, yet in which it can conveniently be made ready for use when the test site is reached. More particularly, the steps involved in getting the apparatus ready for use at a test site and securing it again for travel at the end of a day's testing must be simple, convenient, and foolproof; otherwise, the securing process will be neglected, and the apparatus eventually damaged in travel.

In order that the source and detector can be properly adjustable with respect to the patient, three degree of freedom of motion along orthogonal axes and two degrees of freedom of rotation of the source and detector with respect to the patient are necessary. These requirements pose very substantial design constraints on the unit. Furthermore, these motions of the apparatus must be either powered or made essentially effortless by design of the gantry apparatus.

At the same time, the unit must be safe. For example, a complete power failure may not permit any portion of the apparatus to fall on the patient. Furthermore, and as noted above, the system must be convenient and foolproof in use and must be manufacturable at a reasonable cost if such testing is to be economically feasible.

The prior art does not teach apparatus which is suitable for such purposes. For example, Miyahara et al U.S. Pat. No. 4,503,552 teaches a "simple mounting structure for dental x-ray apparatus" which appears to provide three degree of freedom and at least one degree of rotation. This structure appears to be far too flimsy and insubstantial to be suitable for use in a vehicle. In particular, no means for securing the unit against vibration and road shock during travel is provided.

U.S. Pat. No. 4,694,481 to Tashjian et al shows a transportable x-ray apparatus, but this device does not appear to provide the full range of motion required by the particular x-ray fluorescence test discussed above. Moreover Tashjian et al does not appear to teach any means for securing the x-ray source and detector for travel, which as will appear below is an important aspect of the present invention.

Finally, U.S. Pat. No. 4,181,347 to Clark shows a mobile computerized tomography (CT) unit. This patent simply indicates that the CT equipment is to be mounted on shock vibration-isolation mounts.

SUMMARY OF THE INVENTION

The present invention comprises an improved x-ray gantry in which a first standard is mounted vertically in a vehicle and is shock mounted to the vehicle at both ends. A first carriage moves up and down with respect to the first standard, that is, along the z-axis. Preferably this motion is powered. A horizontal arm is carried by the first carriage. A second carriage moves back and forth on the horizontal arm, that is, along the x-axis, and carries a transverse arm. The transverse arm is movable with respect to the second carriage along the y-axis. The x-ray source and detector are both mounted on a support plate mounted on the transverse arm.

In the preferred embodiment of the invention, the second carriage, the transverse arm, and the support plate are rotatable about the horizontal arm, that is, about the x-axis, and this rotation is powered. Similarly, the support plate may be pivoted with respect to the transverse arm, and this rotation may also be powered. Movement of the support plate, transverse arm and second carriage along the horizontal arm is unpowered, since this motion is essentially horizontal. Linear motion of the transverse arm and support plate with respect to the second carriage is likewise unpowered.

In the preferred embodiment of the invention, five locking devices are provided, each mechanically locking the device with respect to one of the three orthogonal degrees of motion or in one of the two degrees of rotational freedom.

The amount of motion provided by the powered devices is controlled by limit switches. ,The limit switches define fully extended and "home" positions. When it is desired that the vehicle be moved from one location to another, the apparatus is moved into the home position with respect to each of the three orthogonal degrees of freedom and the two rotational degrees of freedom. Two caging arms, pivoted about orthogonal axes with respect to the vehicle, are then fixed directly to the support plate, such that the gantry mechanism is not required to absorb road shock due to the weight of the source and detector assembly.

BRIEF DESCRIPTION OF THE DRAWINGS

The invention will be better understood if reference is made to the accompanying drawings, in which:

FIG. 2 shows an orthogonal view of the arrangement of the plural caging arms employed during transit of the gantry according to the invention;

FIG. 3 shows a detail of the locking mechanism used to lock the caging arms to the support plate;

DESCRIPTION OF THE PREFERRED EMBODIMENTS

Figure 1:
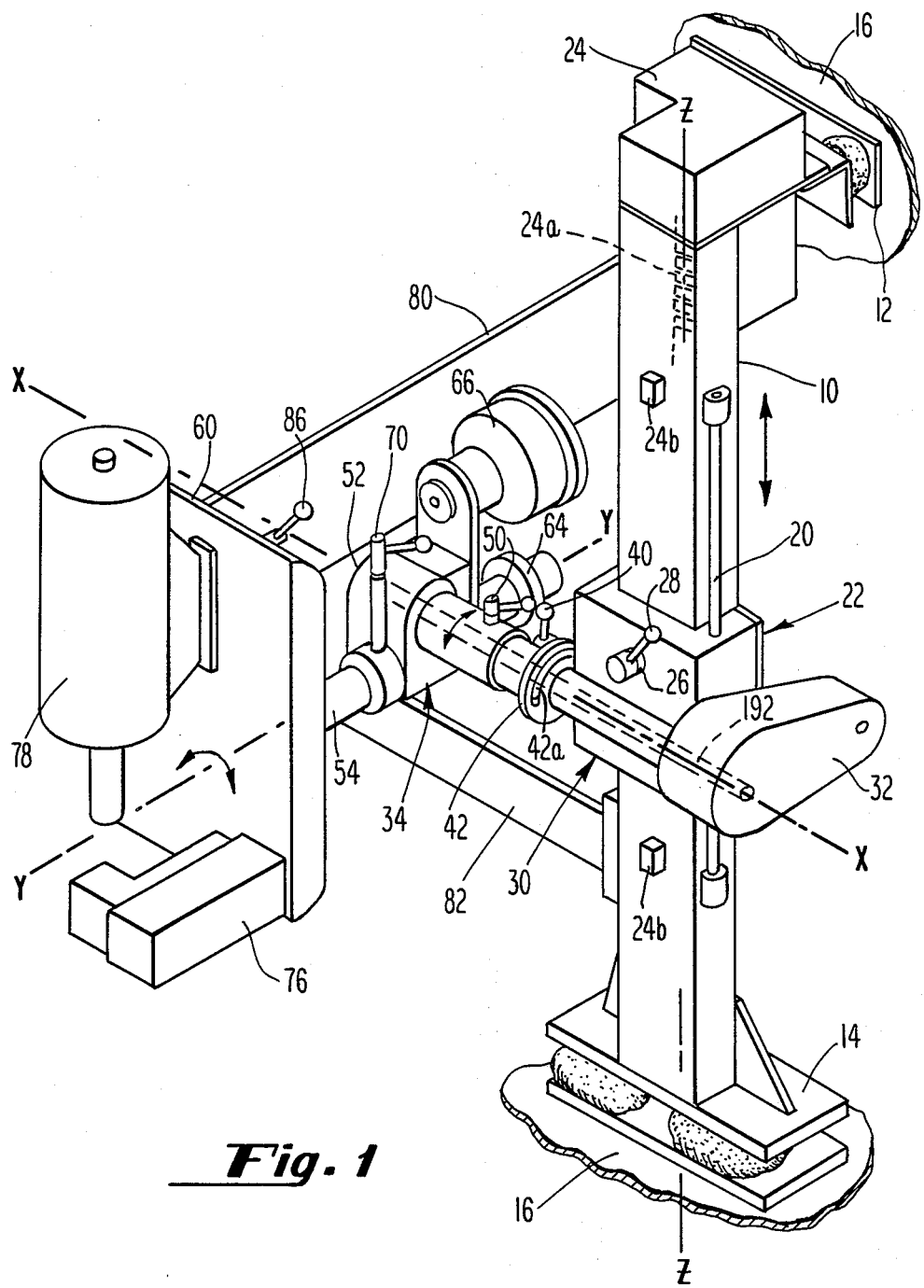
FIG. 1 shows an isometric view of the x-ray gantry of the invention as a whole.

FIG. 1 shows an isometric view of the x-ray gantry apparatus of the invention. A vertical standard 10 is fixed via shock mounts indicated at 12 and 14 to a mounting structure 16, which in the preferred embodiment may comprise the body of a van or other vehicle. In the preferred embodiment, standard 10 is fabricated in box section form of aluminum plates bolted together, but this is not critical to the invention as claimed. Disposed on either side of the standard 10 are guide rods 20 on which a first carriage 22 moves vertically along the z-axis. The carriage 22 is supported on the guide rods 20 by conventional linear bearings. A drive unit 24 rotating a lead screw 24a located within the standard 10 is employed to drive the carriage 22 and the associated x-ray apparatus vertically with respect to standard 10, that is, along the z-axis. A locking member 26 may be provided to lock the first carriage 22 in any desired vertical position, both during patient examinations and for security of the apparatus during travel. The locking device 26 may simply comprise a screw which is tightened by a lever 28 to bear against the face of the standard 10.

The shock mounts 12, 14 can be chosen from a wide variety of commercially available units in accordance with the weight of the unit and its anticipated use in vehicles.

A horizontal arm assembly 30 is mounted on the carriage 22. The horizontal arm assembly comprises a splined shaft 192 (shown in phantom in FIG. 1; see FIG. 5) which extends from a horizontal drive unit 32 into a second carriage indicated generally at 34. The second carriage 34 is mounted to the splined shaft 192 by a linear ball bushing, such that the second carriage 34 is movable along the horizontal shaft 30, that is, along the x-axis. The horizontal arm assembly 30 remains horizontal, such that no motor unit is required to drive the carriage 34 along the x-axis; use of the splined shaft 192 provides low friction movement of the carriage 34 such that minimal effort is required to move the carriage 34 through its travel along the x-axis. The splined shaft 192 is rotatable about the x-axis by the motor unit 32 such that the second carriage 34 and the assembly it carries (to be described below) are likewise pivoted about the x-axis.

The motor unit 32 may comprise an electric motor connected through a gear train or chain reduction unit to the splined shaft 192, possibly by way of an intermediate rigid second shaft. In the preferred embodiment, an electric brake is provided on the shaft 192, such that in the event of failure of the gear train or chain or otherwise the carriage assembly 34 is prevented from unrestrained pivoting. The electric brake may be arranged such that in the event of loss of power to the gantry of the invention, it is actuated to lock shaft 192 and the associated assembly against rotation. See FIG. 5. A locking member 40 is also provided, which comprises a screw extending through an arcuate slot 42a in a sector 42. Thus, when the screw is tightened, either to lock the apparatus for patient examination or for travel, the sector 42 bears against the first carriage 22, restraining the second carriage assembly 34 from rotation about the x-axis. A further lock 50 may be provided to restrain the carriage assembly 34 from motion along the x-axis, again both in use and for travel.

As indicated above, second carriage 34 is supported on the horizontal arm 30 by a linear ball bearing 190 (shown in FIG. 5) which allows it to move freely along the x-axis. The outer race of the linear ball bearing 190 is affixed to a block 52 comprising the principal element of second carriage 34. A second outer race of a second linear ball bearing 154 is also fixed to block 52, and the corresponding splined shaft 150, extending along the y-axis, is an integral part of transverse arm 54. See FIG. 4, described below. In this case, the combination of the splined shaft 150 and the second linear ball bearing 154 within the block 52 permits motion of x-ray apparatus support plate 60 back and forth along the y direction.

In the preferred embodiment, movement of the x-ray support plate 60 and the associate x-ray apparatus along the y-axis is controlled by a hand screw 64 operating a conventional lead screw arrangement. See FIG. 4. This motion is locked by a lock 70 which bears directly on the shaft 54.

Rotation of the x-ray apparatus 76, 78 about the y-axis is provided by rotating the support plate with respect to the splined shaft 150 (see FIG. 4) within arm 54. In a currently preferred embodiment of the invention, a motor is provided for rotating the plate 60 and the associated x-ray apparatus 76, 78 with respect to the shaft 54. This assembly is detailed in connection with FIG. 4. However, it will be recognized by those of skill in the art that alternative arrangements would be possible, and these are believed to be within the scope of the invention where not specifically excluded by the claims hereof. Rotation of the support plate 60 and the associated x-ray apparatus about the y-axis is locked by a further lock member 86 which is detailed below in connection with FIG. 4.

As indicated above, the gantry assembly of the invention is particularly designed for supporting x-ray apparatus for detection of lead toxicity in patients using an x-ray fluorescence technique. This apparatus comprises a source of x-ray energy indicated generally at 76 and a detector indicated at 78. See Wielopolski et al, supra, for further details. However, the utility of the gantry of this invention is not limited to that particular application.

Note that to the extent the y-axis defined by the transverse arm 54 is varied upon rotation of arm 54 about the x-axis, the y-axis is no longer literally "orthogonal" to the z-axis. Reference herein to the "y-axis" is generally meant to refer to the axis defined by arm 54, unless the context indicates otherwise, whether or not this is at any particular time literally at 90 degrees to the z-axis defined by standard 10.

FIG. 1 shows one embodiment of the caging arrangement which is suitable for supporting the support plate 60 of the apparatus of the invention during travel. The caging arrangement includes first and second caging arms, 80 and 82 respectively. In this embodiment, first caging arm 80 is mounted to the mounting structure 16 (which as noted may be a vehicle) by a shock mount or other vibration-damping arrangement. The other end of the caging arm 80 is releasably fixed to the support plate 60 by any manner of convenient, yet rigid locking means. The second caging arm 82 is mounted to the standard 10, again by a shock mount, and its outer end is similarly releasably fixed to the support plate 60. In this way support for the support plate 60 is provided in orthogonal directions, whereby it is rigidly fixed with respect to the vehicle during travel. A second embodiment of the caging arrangement which is presently preferred is shown in connection with FIG. 2.

As noted, FIG. 2 shows the presently preferred embodiment of the caging arrangement. In this case first and second caging arms 100 and 102 are attached to the mounting structure 16 (which, again, may be the body of a vehicle) by shock mounts 104, 106 respectively. As indicated, the caging arm 100, 102 are each hinged to the mounting structure 16 by hinges 100a and 102a, the axes of which are orthogonal to one another. The axis of the hinge 100a of the first caging arm 100 is vertical, such that in order to secure the gantry for transit, the arm 100 is swung outwardly from a position in which it is parallel to the mounting structure 16 to a position at right angles thereto. Caging arm 100 is then rigidly fixed to the support plate 60 by locking assemblies 130, which are discussed below. The axis of hinge 102a by which arm 102 is fixed to the vehicle is horizontal, such that the second caging arm 102 is swung downwardly from a vertical position to the horizontal in order to secure support plate 60 for travel. Arm 102 is then similarly fixed to plate 60 by locking assemblies 130.

As indicated in FIG. 2, in the caged or "home" position as secured for travel, the support plate 60 and the x-ray apparatus indicated generally at 78 are horizontal. In use, the support plate 60 and the x-ray apparatus are typically disposed in a vertical position as shown in FIG. 1. However, the invention is not so limited.

Therefore, when it is desired to arrange the apparatus of the invention for use, the caging arms 100, 102 are detached from the support plate 60, to which they are attached by the structure detailed in connection with FIG. 3 and pivoted to positions against the mounting structure 16, which again may be the wall of a vehicle. The support plate and x-ray apparatus are then moved into a desired position for use.

As will be appreciated by those of skill in the art, the caging arrangement shown in FIG. 2 employing two caging arms with orthogonal pivot axes directly restrains movement of the support plate 60 itself and the associated x-ray apparatus against motion in orthogonal directions. This provides the maximum possible protection of the x-ray apparatus against vibration damage during travel, and avoids reliance on the rigidity of the remaining elements of the gantry of the invention for this restraint during travel.

More specifically, any freely pivoting hinge will allow some motion of the hinged member along the axis of the hinge pivot. By provision of the plural caging arms with orthogonal axes, each arm prevents motion of the support plate along the axis of the other caging arm. In this way, when secured, the support plate 60 together with the caging arms 100 and 102 make up a rigid unit fixed to the support member 16 by the shock mounts 104, 106.

FIG. 3 shows a cross-sectional view along the line 3—3 of FIG. 2, and details a typical locking assembly 130 by which arms 100 and 102 may be releasably fixed to the support plate 60 for travel. In this case, the support plate 60 comprises a side member 110. The caging arm 100 comprises a main member 112, which is stiffened by a second member 114. The main member 112 is juxtaposed to the side member 110 when the caging arm 100 is fixed to the support plate for travel. A threaded locking bolt 116 extends through the main member 112 into a threaded hole in the member 110, locking the two together. Preferably, the bolt extends through a slot 120 in the member 112 permitting some variance of the relative position of the support plate 60 in the home or locked position. The bolt 116 may be retained in the slot 120 by a threaded washer 124. The washer 124 fits within a counterslotted recess 126 in the face of the member 112. The bolt 116 may be fitted with a bar 128 to ease its rotation by the medical technicians who operate the x-ray apparatus, to ensure that the apparatus will be properly caged prior to travel. One or more essentially equivalent locking assemblies 130 may be provided on both caging arms 100, 102, again to ensure that the support plate 60 and the associated x-ray apparatus are appropriately secured to the vehicle itself via shock mounts 104, 106 in transit. The slot on the arm 102 may extend orthogonal to the arm 100 for ease of securing. The tight fitting of the screws and their pivot arrangement with respect to the support plate gives great security to the arrangement. In particular, the washers 126 confine the bolts 116 with respect to the arms 100, 102. Thus, when plural bolts 116 are provided, as on the left side of the assembly of FIG. 2, they must each be tightened or loosened progressively. This provides further security to the arrangement.

Preferably a microswitch 200 is mounted on a bracket 202 such that it is actuated when the bolt 116 is tightened home. The microswitch 202 is connected in circuit as indicated at 204 with an alarm 206 and the ignition of the associated vehicle, such that if the vehicle is moved when the support plate is not caged, the alarm is sounded. This allows the vehicle to be moved quickly, e.g., in emergency situation but would prohibit long drives with the support plate not caged.

Figure 4:
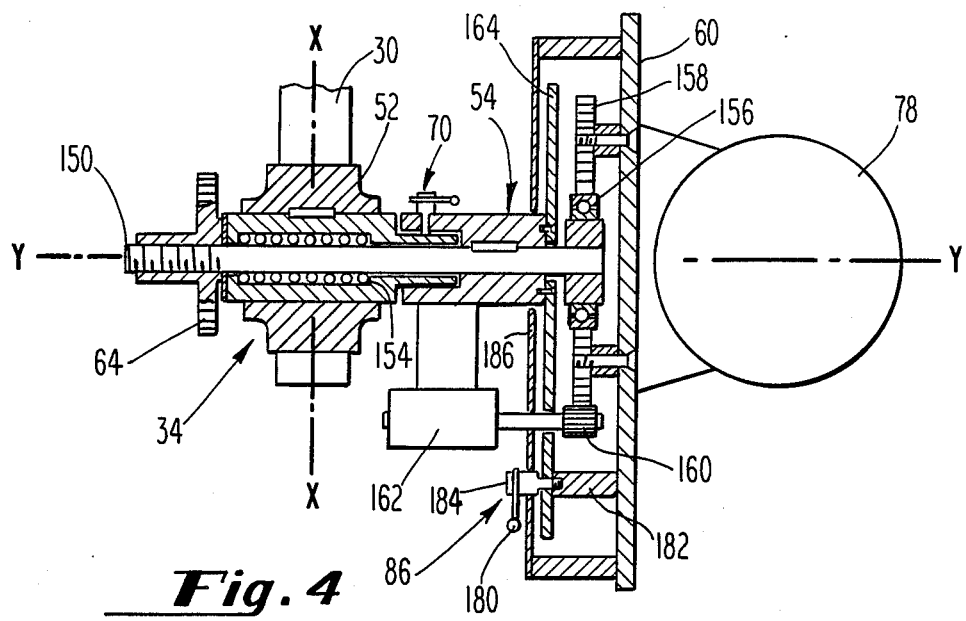
FIG. 4 shows a cross-sectional view taken through the y-axis, as identified in FIG. 1.

FIG. 4 shows a detail of the assembly of the transverse arm 54 and the support plate 60 and the x-ray apparatus 78. FIG. 4 is essentially a cross-section along the y—y axis in FIG. 1; however, some parts have been displaced from their positions in the preferred embodiment of the invention, for clarity of the view. In particular, the horizontal arm 30 is shown beneath the transverse arm 54. As indicated above, the second carriage assembly 34 comprises a block member 52 which receives the horizontal arm 30 and also the transverse arm 54. As indicated above, horizontal arm 30 is rotated by motor assembly 32 to rotate this entire assembly about the x-axis.

As shown in detail in FIG. 4, the transverse arm 54 comprises a second splined shaft 150 which is threaded to a hand screw 64 to move the support plate assembly 60 back and forth along the y-axis, as discussed above. This motion is facilitated by employment of the splined shaft 150 in connection with a second linear ball bushing assembly 154 received within the block 52. Mounted on the end of the splined shaft 150 is a bearing 156, shown as a single ball bearing; plural bearings can be used to reduce the specific loading if desired. To the outer race of this ball bearing is mounted a gear 158, which is engaged with a pinion gear 160 driven by a motor 162, which is fixed to shaft 54. A plate. 164 is also fixed to the shaft 54 by screws 166. The support plate 60 is mounted on gear 158 as shown, such that when the motor 162 is energized, the support plate 60 and the associated x-ray apparatus 78 are pivoted about the y-axis.

A locking assembly 86 is provided to lock the support plate 60 against rotation, during patient examination and during movement of the device. This assembly 86 comprises a bolt 184 which extends through an arcuate slot in plate 164 and is threaded into a post 182 fixed to the support plate 60. Bolt 184 frictionally engages the stationary plate 164 against the post 182 when tightened by rotation of handle 180. A cover plate 186 rotating with plate 60 may be provided to keep the patient's hair, clothing, jewelry, etc. out of the gear assembly and to prevent entry of dust.

A similar locking assembly 70 is provided to lock the motion of transverse arm 54 with respect to the second carriage 34.

The assembly shown in FIG. 4 thus provides hand screw adjustment of the position of the support plate 60 along the y-axis and allows rotation of the support plate 60 with respect to shaft 54, that is, rotation about the y-axis. As discussed above, it would also be possible to power the motion of the shaft 54 along the y-axis, but this would substantially complicate the actual construction of the device and is, therefore, not provided in the presently preferred embodiment of the invention. A counterweight 66 (FIG. 1) is provided opposite the x-ray apparatus 78 to limit the physical effort required to move this assembly along the y-axis.

Figure 5:
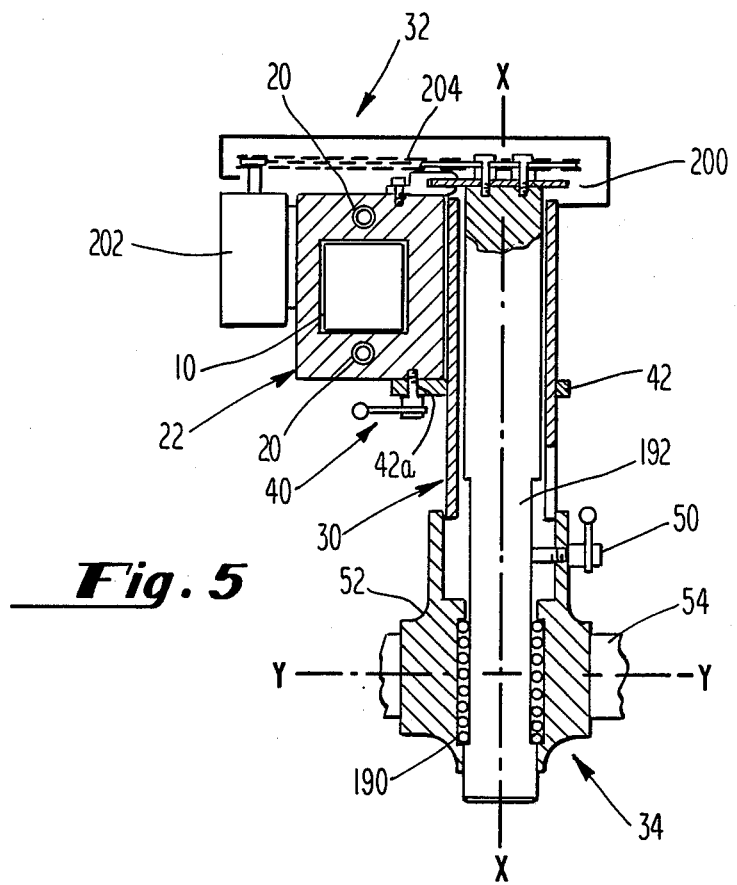
FIG. 5 shows a cross sectional view through a portion of the x-axis, as identified in FIG. 1.

FIG. 5 shows a view through a portion of the x-axis, illustrating the manner in which the second carriage 34 is assembled to the horizontal arm 30. A linear splined member 192 runs within the horizontal arm 30. Block 34 rides on splined member 192 by way of recirculating linear ball bushing 190. This allows very easy movement of the entire assembly carried by the second carriage 34, including the support plate 60, the x-ray apparatus 78, the transverse arm 54, and the counter weight 66 (FIG. 1), along the horizontal arm 30. Clamp 50 locks the second carriage assembly 34 at any desired position along the horizontal bar 30.

Motor assembly 32, comprising a motor 202 and a chain drive 204, is connected to the splined member 192 to rotate the horizontal arm 30, the second carriage 34, and the associated apparatus. An electric brake 200 is provided to lock member 192 to first carriage 22. The brake 200 may be arranged to lock the member 192 upon failure of the motor unit 32 by shearing a key, for example, in the chain drive 204. This prevents the x-ray apparatus 78 from falling on the patient. Lock 40 has the same function. The electric brake 200 may be arranged to lock member 192 to first carriage 22 upon loss of electrical power to the device.

Preferably the electric brake 200 is functionally connected to the ignition of the vehicle in which the gantry of the invention is employed, so that if the ignition is "on" the brake is locked. The other electrical controls of the gantry may similarly be disabled unless the ignition of the vehicle is "off".

Preferably a patient chair is associated with the x-ray apparatus of the invention, and comprises a back, a seat, a cradle for receiving the patient's leg, and a foot clamp for maintaining the foot and tibia in a fixed position during the examination. Preferably the seat and back are tiltable and adjustable for height with respect to the cradle, and the overall assembly is also adjustable for height, thus providing substantially unlimited patient position adjustment for the convenience of the technicians operating the x-ray apparatus associated with the gantry of the invention.

While a preferred embodiment of the invention has been described in detail, it will be appreciated by those of skill in the art that there are numerous alternatives and improvements thereto which can be made and which are intended to be encompassed within the scope of the invention.

For example, it would be possible to drive the gantry of the invention through each of its three degrees of freedom in orthogonal directions, as well as through its two degrees of rotational freedom. Similarly, there are additional features which can conveniently be added. In a preferred embodiment of the invention, each of the motions of the gantry which is powered is controlled by limit switches, such that the limit switches define the "home" (i.e., caged for transit) and fully extended positions. Exemplary limit switches 24b are shown in FIG. 1. Accordingly, when it is desired to return the apparatus to its home position for transit the operator simply sets all the drive motors to move the device toward the home position. When the home position is reached, the limit switches cause the motors to stop, such that the device is automatically in its home position with respect to all powered dimensions of motion. This provides substantial operator convenience, and further aids in the long-term reliability of the gantry of the invention by simplification of the caging arrangement.

Many alternative arrangements of the drive devices as well as the support members and the like of the apparatus of the invention are considered to be within the skill of the art, given the disclosure of the invention provided above, as are the details of its construction, where not described specifically above.

For example, in the above, the second carriage moves along the horizontal arm to provide movement along the x-axis. It would be equivalent to move the horizontal arm with respect to the first carriage. Similarly, the transverse arm moves with respect to the second carriage to provide movement of the support plate along the y-axis. It would be equivalent to move the support plate with respect to the transverse arm. Where the functional limitations of the following claims do not require otherwise, they are to be read as including these and like equivalents of the structure described.

Therefore, while a preferred embodiment of the invention has been described in detail, this is not to be considered a limitation on the invention but merely as exemplary thereof. Instead, the invention is to be limited only by the following claims.

I claim:

1. A gantry apparatus for positively supporting an x-ray device while permitting adjustment of the position of the device with respect to a patient to be examined, comprising:

a standard fixed with respect to a mounting structure, and defining a path of movement along a first z-axis;

a first carriage means, movable with respect to said standard along said z-axis, and lockable to said standard;

a horizontal arm, fixed to said first carriage means and defining a second path of movement along a second x-axis orthogonal to said first z-axis;

second carriage means, movable with respect to said standard along said x-axis, and defining a third transverse y-axis of motion orthogonal to said x- and z-axes;

a transverse arm, mounted to said second carriage means and extending along said y-axis;

a support plate means mounted to said transverse arm for movement along said y-axis and comprising means for supporting the x-ray device; and caging arm means comprising plural caging arms extending from plural points fixed with respect to said mounting structure to said support plate means, said caging arm means being releasably lockable to said support plate means while said support plate means is in a defined home position.

2. The apparatus of claim 1 wherein said caging arms extend to said support plate means from said mounting structure in substantially orthogonal directions.

3. The apparatus of claim 1 wherein said caging arms are hinged to said mounting structure along substantially orthogonal axes.

4. The apparatus of claim 1 further comprises a source of x-rays and a detector of fluoresced photons.

5. The apparatus of claim 1 wherein said z-axis is vertical, and further comprising means for driving said first carriage means with respect to said standard.

6. The apparatus of claim 5 wherein said means for driving comprises a lead screw driven by a motor fixed with respect to said standard.

7. The apparatus of claim 1, wherein said first and second carriage means and said support plate means are each movable along their respective axes of motion between predetermined home and full extension positions.

8. The apparatus of claim 7 wherein said caging arms are lockable to said support plate means only when each of said first and second carriage means and said support plate are in their home positions.

9. The apparatus of claim 8, wherein the movement of at least one of said first and second carriage means and said support plate means along their orthogonal axes is powered, and further comprising means for automatically halting the powered movement thereof at the home and full extension positions.

10. The apparatus of claim 1, further comprising means for permitting rotation of said support plate means and the transverse arm about said x-axis.

11. The apparatus of claim 10 wherein said x-axis is horizontal.

12. The apparatus of claim 11, further comprising counter-weight means disposed opposite said support plate means with respect to said x-axis.

13. The apparatus of claim 12, further comprising means for locking said transverse arm against rotation about said x-axis.

14. The apparatus of claim 13, further comprising means for permitting rotation of said support plate means about the y-axis.

15. The apparatus of claim 14, further comprising means for locking said support plate means against rotation about said y-axis.

16. The apparatus of claim 15, further comprising means for powering the rotation of said support plate means about said y-axis.

17. The apparatus of claim 1, comprising means for mounting said apparatus to a vehicle.

18. The apparatus of claim 17, wherein said means for mounting comprises shock-mount means permitting a limited amount of damped motion of said standard with respect to said vehicle.

19. The apparatus of claim 17, wherein said plural caging arms are attached to said means for mounting by hinges attached to said vehicle by shock-mount means permitting a limited amount of damped motion of said caging arms with respect to said vehicle.

20. A gantry apparatus for positively supporting an inspection device while permitting adjustment of the position of the device with respect to an object to be inspected, comprising:

a first standard fixed with respect to a mounting structure, and defining a path of movement along a first z-axis;

a first carriage means, movable with respect to said first standard along said z-axis;

a horizontal arm, fixed to said first carriage means and defining a second path of movement along a second x-axis orthogonal to said z-axis;

a second carriage means, movable with respect to said horizontal arm, and defining a third y-axis of motion;

a transverse arm, extending along said y-axis;

support plate means mounted to said transverse arm for supporting the inspection device; and caging arm means comprising plural arms extending from plural points fixed with respect to said mounting structure to said support plate means, said caging arms being releasably lockable to said support plate means while said support plate means is in a defined home position.

* * * * *